United States Patent
Yoon et al.

(10) Patent No.: US 9,562,216 B2
(45) Date of Patent: Feb. 7, 2017

(54) MICROFLUIDIC PLATFORM FOR CELL CULTURING, AND CELL CULTURING METHOD USING SAME

(75) Inventors: Seung Yong Yoon, Seoul (KR); Se Gyeong Joo, Seoul (KR); Ha Lim Song, Seoul (KR); Dong Hou Kim, Seoul (KR)

(73) Assignee: UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 429 days.

(21) Appl. No.: 14/233,759

(22) PCT Filed: Jul. 3, 2012

(86) PCT No.: PCT/KR2012/005278
§ 371 (c)(1),
(2), (4) Date: Jan. 20, 2014

(87) PCT Pub. No.: WO2013/012188
PCT Pub. Date: Jan. 24, 2013

(65) Prior Publication Data
US 2014/0141514 A1    May 22, 2014

(30) Foreign Application Priority Data
Jul. 20, 2011 (KR) .................. 10-2011-0071996

(51) Int. Cl.
| C12N 5/0793 | (2010.01) |
| C12N 5/02 | (2006.01) |
| C12M 3/06 | (2006.01) |
| C12M 1/00 | (2006.01) |

(52) U.S. Cl.
CPC ............ C12N 5/0619 (2013.01); C12M 23/16 (2013.01); C12M 23/34 (2013.01)

(58) Field of Classification Search
CPC ....... C12N 5/0619; C12M 23/16; C12M 23/34
USPC ........................................................ 435/383
See application file for complete search history.

(56) References Cited

U.S. PATENT DOCUMENTS

2009/0023608 A1*  1/2009  Hung ................ B01L 3/502707
                                                                506/32

FOREIGN PATENT DOCUMENTS

KR    10-2008-0071786        8/2008

OTHER PUBLICATIONS

Park, Jae Won et al., Microfluidic compartmentalized co-culture platform for CNS axon myelination research, Biomed Microdevices (2009) vol. 11, No. 6, pp. 1145-1153.

(Continued)

Primary Examiner — Michael Hobbs
(74) Attorney, Agent, or Firm — Revolution IP

(57) ABSTRACT

Provided are a microfluidic platform for cell culturing and a cell culturing method using the same. By applying a structure of a compartment which surrounds at least a portion of an annular reservoir and moving cells to be cultured to a site adjacent to a microchannel via rotation, a probability of observing cells that grew after culturing may increase and a probability of causing cells, particularly neurons, to grow so as to correspond to a signal transfer direction may increase.

17 Claims, 7 Drawing Sheets

(56) References Cited

OTHER PUBLICATIONS

Park, Jae Won et al., A Multi-compartment CNS Neuron-glia Co-culture Microfluidic Platform, Journal of Visualized Experiments (2009) vol. 31, e1399.

Majumdar, D et al., Co-culture of neurons and glia in a novel microfluidic platform, Journal of Neuroscience Methods (Mar. 15, 2011) vol. 196, pp. 38-44.

* cited by examiner

MICROFLUIDIC PLATFORM FOR CELL CULTURING, AND CELL CULTURING METHOD USING SAME

CROSS REFERENCE TO PRIOR APPLICATIONS

This application is a National Stage Application of PCT International Patent Application No. PCT/KR2012/005278 filed on Jul. 3, 2012, under 35 U.S.C. §371, which claims priority to Korean Patent Application No. 10-2011-0071996 filed on Jul. 20, 2011, which are all hereby incorporated by reference in their entirety.

TECHNICAL FIELD

The present invention relates to a microfluidic platform for cell culturing, and more particularly, to a microfluidic platform for cell culturing and a cell culturing method, wherein cells, such as neurons, are cultured to observe growth of the cells and interactions between cells for signal transference are observed and experimented.

BACKGROUND ART

Generally in neurobiology fields, a microfluidic platform is used to observe and experiment growth of neurons and interactions between cells.

FIG. 1 is a diagram of a general structure of a neuron. Referring to FIG. 1, the neuron includes a cell body 1 including a nucleus 1a, a plurality of dendrites 2 growing from the cell body 1 and receiving a signal from an adjacent neuron, and an axon 3 growing from the cell body 1 and transmitting a signal to an adjacent neuron.

FIGS. 2 and 3 illustrate an example of a general microfluidic platform 10 applied to experiment the neuron of FIG. 1 (disclosed in Park J, Koito H, Li J, Han Microfluidic compartmentalized co-culture platform for CNS axon myelination research, Biomed Microdevices. 2009 Dec.; 11(6):1145-53).

As shown in FIGS. 2 and 3, the general microfluidic platform 10 includes, at one side, a pair of first reservoirs 11 spaced apart from each other and a soma compartment 12 communicating between the pair of first reservoirs 11. The general microfluidic platform 10 further includes, at the other side, a pair of second reservoirs 21 facing the pair of first reservoirs 11, and an axon compartment 22 communicating between the pair of second reservoirs 21. Also, the soma compartment 12 and the axon compartment 22 communicate with each other through a plurality of microchannels 30.

The general microfluidic platform 10 described above may be manufactured by completing a mater mold (not shown) having male shapes respectively corresponding to the first and second reservoirs 11 and 21, the soma and axon compartments 12 and 22, and the microchannels 30, pouring polydimethylsiloxane (PDMS) satisfactorily mixed with a catalyst into the master mold, and hardening the PDMS at about 75° C. Here, the pair of first reservoirs 11 and the pair of second reservoirs 21 are punched, and a cover glass is attached to the first and second reservoirs 11 and 21 and then coated so as to set conditions for culturing neurons. While culturing the neurons, the general microfluidic platform 10 is maintained to be wet therein.

The first and second reservoirs 11 and 21 contain neurons to be cultured, and are substantially used to supply and replace a culture medium. The soma and axon compartments 12 and 22 have a height of about 100 μm, and are spaced in which the neurons are stably cultured. The axon 3 of FIG. 1 grown by culturing the neuron passes through the microchannel 30. Here, the neuron at initial culturing has a round millet shape, and if a width and height of the microchannel 30 are high, the neuron may move to the axon compartment 22 on the opposite side. Thus, the microchannel 30 may have a height from about 2.5 to about 3 μm and a width per channel of about 10 μm so as to prevent the neuron from moving to an opposite compartment. In other words, in the soma compartment 12, the neuron is initially cultured and the cell body 1 including the nucleus 1a is located. Also, in the axon compartment 22, the axon 3 that passed through the microchannel 30 is located.

However, in the general microfluidic platform 10, initial neurons put into the first reservoir 11 move to and are randomly distributed in the soma compartment 12 with the culture medium. Here, the axon 3 of the initial neuron adjacent to the microchannel 30 may pass through the microchannel 30 and grown towards the axon compartment 22 located at the other side, but the axon 3 of the initial neuron that is not adjacent to the microchannel 30 may not pass through the microchannel 30 and may grow only inside the soma compartment 12. In other words, since the initial neurons are randomly distributed in the soma compartment 12, the number of axons passing through the microchannels 30 from among the initial neurons put into the first reservoir 11 may be low, and thus a probability of observing the axons 3 for an experiment may also be low.

Meanwhile, in order to perform an experiment corresponding to a signal transfer direction of the neuron, the axon 3 that passed through the microchannel 30 from the soma compartment 12 may form a synapse with the dendrite 2 of the neuron cultured in the axon compartment 22.

However, in the general microfluidic platform 10, the axon 3 of the neuron adjacent to the microchannel 30 from among the neurons supplied from the second reservoir 21 and cultured in the axon compartment 22 frequently passes through the microchannel 30 and forms a synapse with the dendrite 2 of the neuron cultured in the soma compartment 12. Accordingly, a probability of growing cells to correspond to a signal transfer direction is low, and it is difficult to secure a required experiment target.

DETAILED DESCRIPTION OF THE INVENTION

Technical Problem

The present invention provides a microfluidic platform for cell culturing and a cell culturing method using the same, wherein a probability of observing cells grown after culturing is increased and cells grow to correspond to a signal transfer direction of the cells.

Technical Solution

According to an aspect of the present invention, there is provided a microfluidic platform for cell culturing and a cell culturing method using the same, wherein the microfluidic platform includes: a first reservoir including a first supply unit that has an annular empty space with an opened top surface such that a first cell to be cultured and a culture medium are supplied; a first compartment including a first culture unit that has an annular empty space surrounding at least a portion of the first supply unit to communicate with the first supply unit such that the first cell supplied from the supply unit is cultured in the culture medium; at least one second reservoir disposed at one side of the first reservoir and including a second supply unit that has an annular empty space with an opened top surface such that a second cell to be cultured and a culture medium are supplied; a second compartment including a second culture unit that communicates with the second supply unit and has a partially annular empty space by surrounding a portion of the first compartment at an interval such that the second cell supplied from the second supply unit is cultured in the culture medium; a first channel unit wherein a plurality of first microchannels communicating the first compartment and the second compartment are annularly arranged; and a first communicating unit including a first communicating path communicating the at least one second reservoir and the second compartment.

Advantageous Effects

According to a microfluidic platform for cell culturing and a cell culturing method using the same of the present invention, a structure of a compartment surrounding at least a portion of an annular reservoir is applied and cells to be cultured are moved adjacent to a microchannel via rotation, and thus a probability of observing cells, for example, axons of neurons, grown after culturing may be increased.

Also, since a probability of growing cells to correspond to a signal transfer direction of the cells is increased, an experiment target required for an experiment may be easily secured. In other words, in neurons, experimental observation targets of sequentially forming synapses between axons and dendrites according to a signal transfer direction may be easily secured.

BEST MODE

Figure 1:
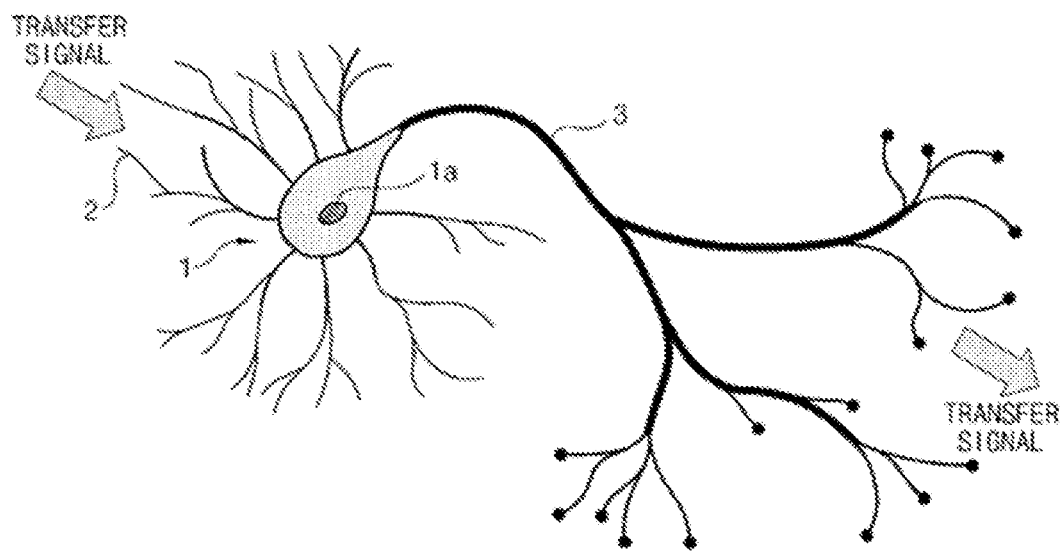
FIG. 1 is a diagram of a general structure of a neuron.
Figure 2:
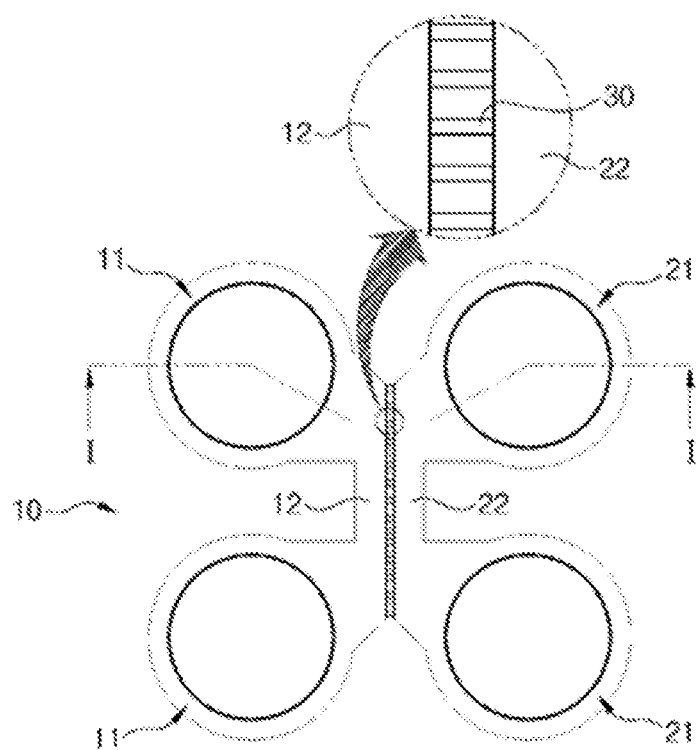
FIG. 2 is a plan view of an example of a general microfluidic platform applied to experiment the neuron of FIG. 1.
Figure 3:
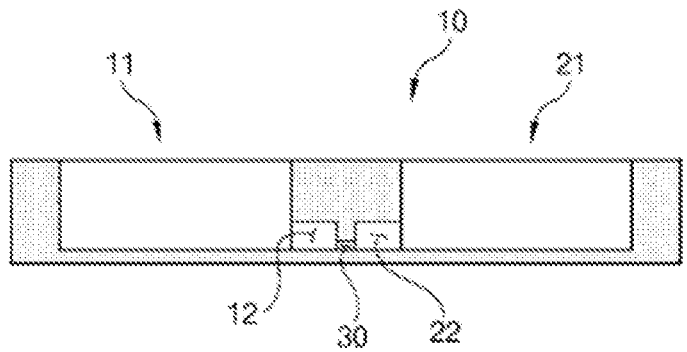
FIG. 3 is a cross-sectional view taken along a line I-I of FIG. 2.

According to an aspect of the present invention, there is provided a microfluidic platform for cell culturing, including: a first reservoir including a first supply unit that has an annular empty space with an opened top surface such that a first cell to be cultured and a culture medium are supplied; a first compartment including a first culture unit that has an annular empty space surrounding at least a portion of the first supply unit to communicate with the first supply unit such that the first cell supplied from the supply unit is cultured in the culture medium; at least one second reservoir disposed at one side of the first reservoir and comprising a second supply unit that has an annular empty space with an opened top surface such that a second cell to be cultured and a culture medium are supplied; a second compartment including a second culture unit that communicates with the second supply unit and has a partially annular empty space by surrounding a portion of the first compartment at an interval such that the second cell supplied from the second supply unit is cultured in the culture medium; a first channel unit wherein a plurality of first microchannels communicating the first compartment and the second compartment are annularly arranged; and a first communicating unit including a first communicating path communicating the at least one second reservoir and the second compartment.

According to another aspect of the present invention, there is provided a cell culturing method including: preparing the microfluidic platform; supplying a first cell and a culture medium to the first reservoir; moving the first cell supplied from the first reservoir to be adjacent to the first microchannel of the first channel unit from the first compartment by rotating the microfluidic platform to generate a centrifugal force; culturing the first cell in the first compartment; supplying a second cell and a culture medium to the at least one second reservoir; moving the second cell supplied from the at least one second reservoir to be spaced apart from the first microchannel of the first channel unit from the second compartment by rotating the microfluidic platform to generate a centrifugal force; and culturing the second cell in the second compartment.

The microfluidic platform may further include: at least one third reservoir disposed at the other side of the first reservoir and including a third supply unit that has an annular empty space with an opened top surface such that a third cell to be cultured and a culture medium are supplied; a third compartment including a third culture unit that communicates with the third supply unit and has a partially annular empty space by surrounding a portion of the second compartment at an interval such that the third cell supplied from the third supply unit is cultured in the culture medium; a second channel unit wherein a plurality of second microchannels communicating the second compartment and the third compartment are annularly arranged; and a second communicating unit including a second communicating path communicating the at least one third reservoir and the third compartment.

According to another aspect of the present invention, there is provided a cell culturing method including: preparing the microfluidic platform above; supplying a first cell and a culture medium to the first reservoir; moving the first cell supplied to the first reservoir to be adjacent to the first microchannel of the first channel unit from the first compartment by rotating the microfluidic platform to generate a centrifugal force; culturing the first cell in the first compartment; supplying a second cell and a culture medium to the at least one second reservoir; moving the second cell supplied to the at least one second reservoir to be adjacent to the second microchannel of the second channel unit from the second compartment by rotating the microfluidic platform to generate a centrifugal force; culturing the second cell in the second compartment; supplying a third cell and a culture medium to the at least one third reservoir; moving the third cell supplied to the at least one third reservoir to be spaced apart from the second microchannel of the second channel unit from the second compartment by rotating the microfluidic platform to generate a centrifugal force; and culturing the third cell in the third compartment.

MODE OF THE INVENTION

Hereinafter, the present invention will be described more fully with reference to the accompanying drawings, in which exemplary embodiments of the invention are shown.

Figure 4:
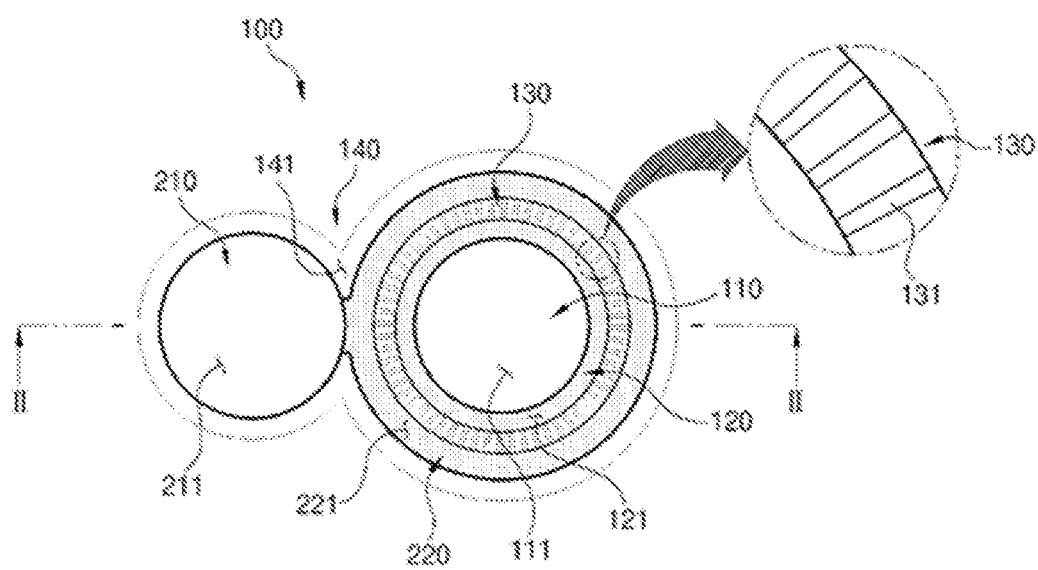
FIG. 4 is a plan view of a microfluidic platform according to an embodiment of the present invention.
Figure 5:
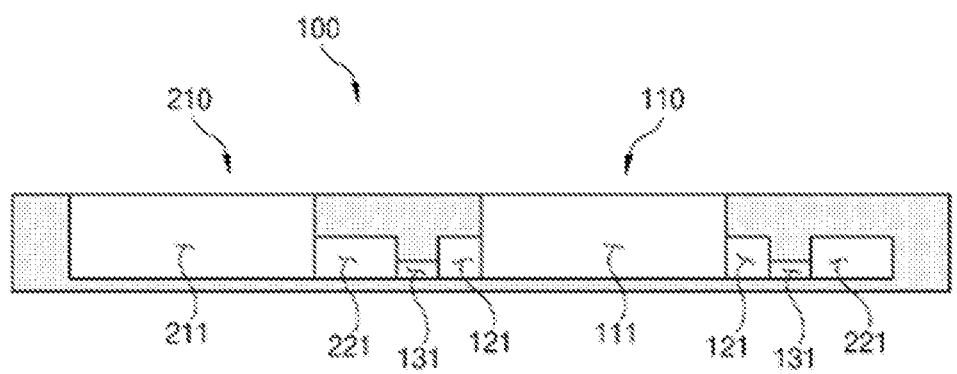
FIG. 5 is a cross-sectional view taken along a line II-II of FIG. 4.

FIG. 4 is a plan view of a microfluidic platform 100 according to an embodiment of the present invention, and FIG. 5 is a cross-sectional view taken along a line II-II of FIG. 4.

Referring to FIGS. 1, 4, and 5, the microfluidic platform 100 includes a first reservoir 110, a first compartment 120, at least one second reservoir 210, a second compartment 220, a first channel unit 130, and a first communication unit 140. Here, the microfluidic platform 100 may be manufactured by completing a master mold (not shown) having male shapes respectively corresponding to the first and second reservoirs 110 and 210, the first and second compartments 120 and 220, the first channel unit 130, and the first communicating unit 140, pouring polydimethylsiloxane (PDMS) satisfactorily mixed with a catalyst into the master mold, and hardening the PDMS at about 75° C.

The first reservoir 110 includes a first supply unit 111 that has an annular empty space with an opened top surface such that a first cell to be cultured and a culture medium are supplied. Here, the first reservoir 110 is a place into which the first cell to be cultured is put and where the culture medium is substantially supplied and replaced.

The first compartment 120 includes a first culture unit 121 that has an annular empty space surrounding at least a portion of the first supply unit 111 to communicate with the first supply unit 111. In the first culture unit 121, the first cell supplied from the first supply unit 111 is cultured in the culture medium. Also, the first compartment 120 has a height of about 100 μm and the first cell is stably cultured therein.

Figure 9:
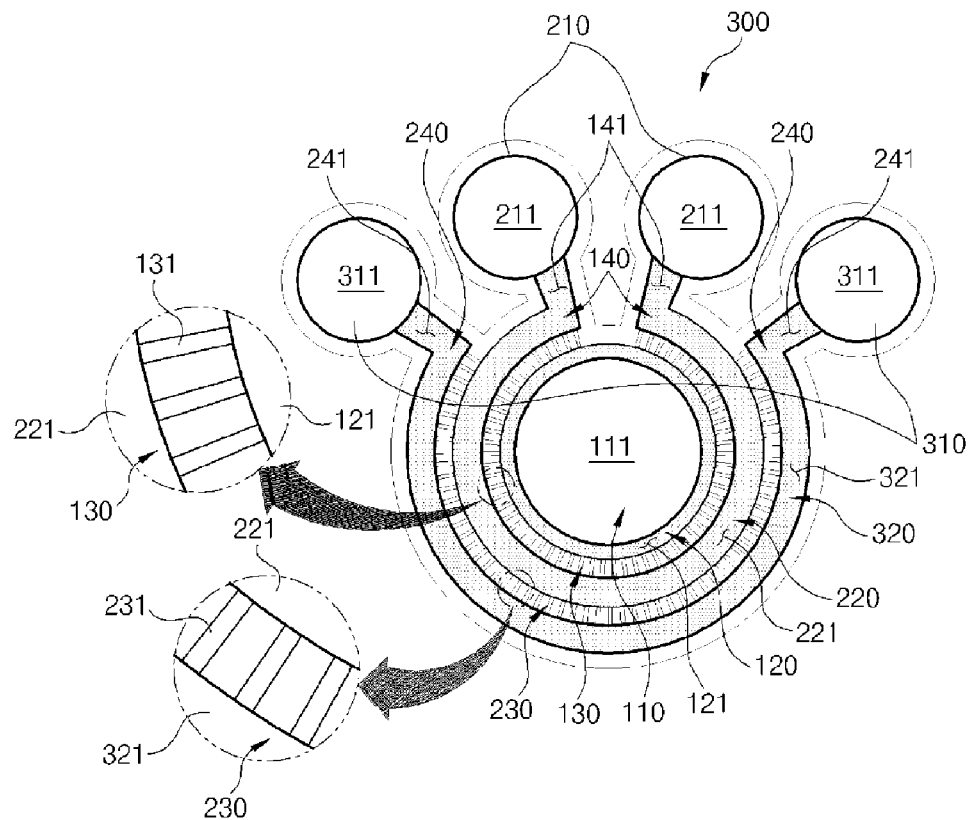
Figure 10:
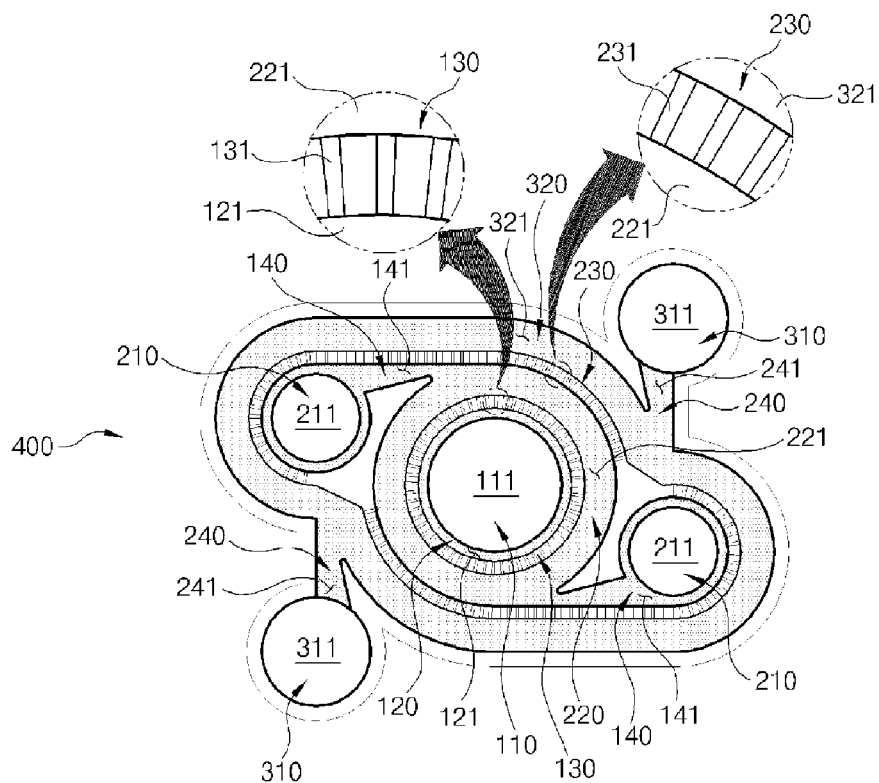

The second reservoir 210 is disposed at one side of the first reservoir 110. The second reservoir 210 includes a second supply unit 211 that has an annular empty space with an opened top surface such that a second cell to be cultured and a culture medium are supplied. In FIGS. 4 and 5, one second reservoir 210 is provided, but alternatively, a plurality of the second reservoirs 210 may be provided as shown in FIGS. 9 and 10 as will be described later. Here, the second reservoir 210 is a place into which the second cell to be cultured is put where the culture medium is substantially supplied and replaced.

The second compartment 220 includes a second culture unit 221 that communicates with the second supply unit 221 and has a partially annular empty space by surrounding a portion of the first compartment 120 at an interval. Also, in the second culture unit 221, the second cell supplied from the second supply unit 221 is cultured in the culture medium. The second compartment 220 also has a height of about 100 μm, and the second cell is stably cultured therein.

In the first channel unit 130, a plurality of microchannels 131 communicating the first and second compartments 120 and 220 are annularly arranged. Here, when the first and second cells are neurons, the axon 3 of FIG. 1 grown by culturing the neuron passes through the first microchannel 131. Here, the neuron at initial culturing has a round millet shape, and if a width and height of the first microchannel 131 are high, the neuron may move to the second compartment 220 on the opposite side. Thus, the first microchannel 131 may have a height from about 2.5 to about 3 μm, a width per channel of about 10 μm, and a length of about 500 to 600 μm so as to prevent the neuron from moving to the second compartment 220. In other words, in the first compartment 120, the neuron is initially cultured and the cell body 1 including the nucleus 1a is located. Also, in the second compartment 220, the axon 3 that passed through the first microchannel 131 of the first channel unit 130 is located.

The first communicating unit 140 includes a first communicating path 141 that communicates the second reservoir 210 and the second compartment 220. Accordingly, the second cell supplied to the second reservoir 210 moves to the second compartment 220 through the first communicating path 141 of the first communicating unit 140 with the culture medium to be cultured.

Figure 12:
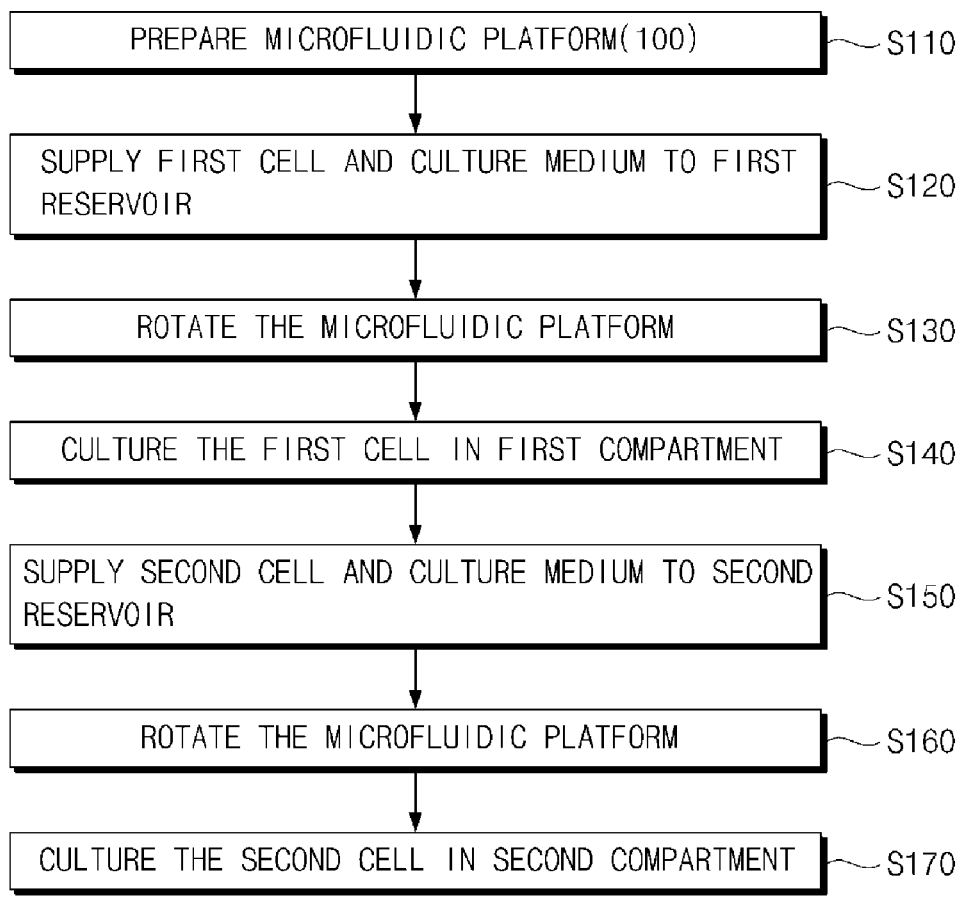
FIG. 12 is a flowchart illustrating a cell culturing method using the microfluidic platform of FIGS. 4 and 5.

Hereinafter, a cell culture method using the microfluidic platform 110 described above will be described with reference to FIGS. 1, 4, 5, and 12. FIG. 12 is a flowchart illustrating a cell culturing method using the microfluidic platform 100 of FIGS. 4 and 5.

First, referring to FIGS. 1, 4, 5, and 12, the microfluidic platform 100 is prepared in operation S110. Here, the first reservoir 110 of the microfluidic platform 100 is punched, and a cover glass is attached to the first reservoir 110 and then coated so as to set conditions for culturing a cell.

When the microfluidic platform 100 is prepared, the first cell and the culture medium are supplied to the first reservoir 110 in operation S120. Here, the first cell may be an initial neuron having a round millet shape, and at this time, the first cell may be the cell body 1 including the nucleus 1a. Also, the inside of the microfluidic platform 100 maintains a wet state during a following culture process.

Next, the microfluidic platform 100 is rotated to generate a centrifugal force. Accordingly, the first cell supplied to the first reservoir 110 is moved to be adjacent to the first microchannel 131 of the first channel unit 130 in the first compartment 120 in operation S130. The microfluidic platform 100 is rotated by using a turn table, but a device for rotating the microfluidic platform 100 is not limited to the turn table as long as the microfluidic platform 100 is rotated at a uniform speed.

Then, the first cell is cultured in the first compartment 120 in operation S140. When the first cell is the neuron, the axon 3 of the neuron cultured in the first compartment 120 grows and passes through the first microchannel 131 of the first channel unit 130. As such, the axon 3 that passed through the first microchannel 131 is located in the second compartment 220.

When the first cell is supplied to the first reservoir 110 and cultured in the first compartment 120 for about one week, the second cell and the culture medium are supplied to the second reservoir 210 in operation S150. Here as well, the second cell may be an initial neuron having a round millet shape, and the inside of the microfluidic platform 100 maintains a wet state during a following culture process.

Then, the microfluidic platform 100 is rotated to generate a centrifugal force, thereby moving the second cell supplied to the second reservoir 210 to be spaced apart from the first microchannel 131 of the first channel unit 130 in the second compartment 220, in operation S160. Here as well, the microfluidic platform 100 is rotated by using a turn table, and a device for rotating the microfluidic platform 100 is not limited as long as the microfluidic platform 100 is rotated at a uniform speed.

Lastly, the second cell is cultured in the second compartment 220 in operation S170. Here as well, when the second cell is the neuron, the dendrite 2 grown from the cell body 1 in the second compartment 220 forms a synapse with the axon 3 that grew in the first compartment 120 and passed through the first microchannel 131.

As described above, according to the cell culturing method using the microfluidic platform 100, the first and second compartments 120 and 220 surround at least a portion of the first reservoir 110, and the first cell is moved adjacent to the first microchannel 131 and the second cell is moved to be spaced apart from the first microchannel 131 by rotating the microfluidic platform 100 to generate the centrifugal force, thereby increasing a probability of observing the cell grown in the first compartment, for example, the axon 3 of the neuron. Moreover, since a probability of growing the cell to correspond to a signal transfer direction of the cell is increased, it is easy to secure an experiment target required for an experiment. In other words, in case of the neuron, an experimental observation target for sequentially forming synapses between the axons 3 and the dendrites 2 according to the signal transfer direction may be easily secured in the second compartment 220.

Meanwhile, the inside of the microfluidic platform 100 has to maintain a wet state during a culture process. Thus, an amount of the culture medium supplied to the first reservoir 110 is set to be higher than an amount of the culture medium supplied to the second reservoir 210 so that a flow of the culture medium from the first compartment 120 to the second compartment 220 is maintained. For example, the amount of the culture medium supplied to the second reservoir 210 may be less than the amount of the culture medium supplied to the first reservoir 110 by about 10%.

A microfluidic platform 200 according to another embodiment of the present invention will now be described with reference to FIGS. 6 and 7.

Figure 6:
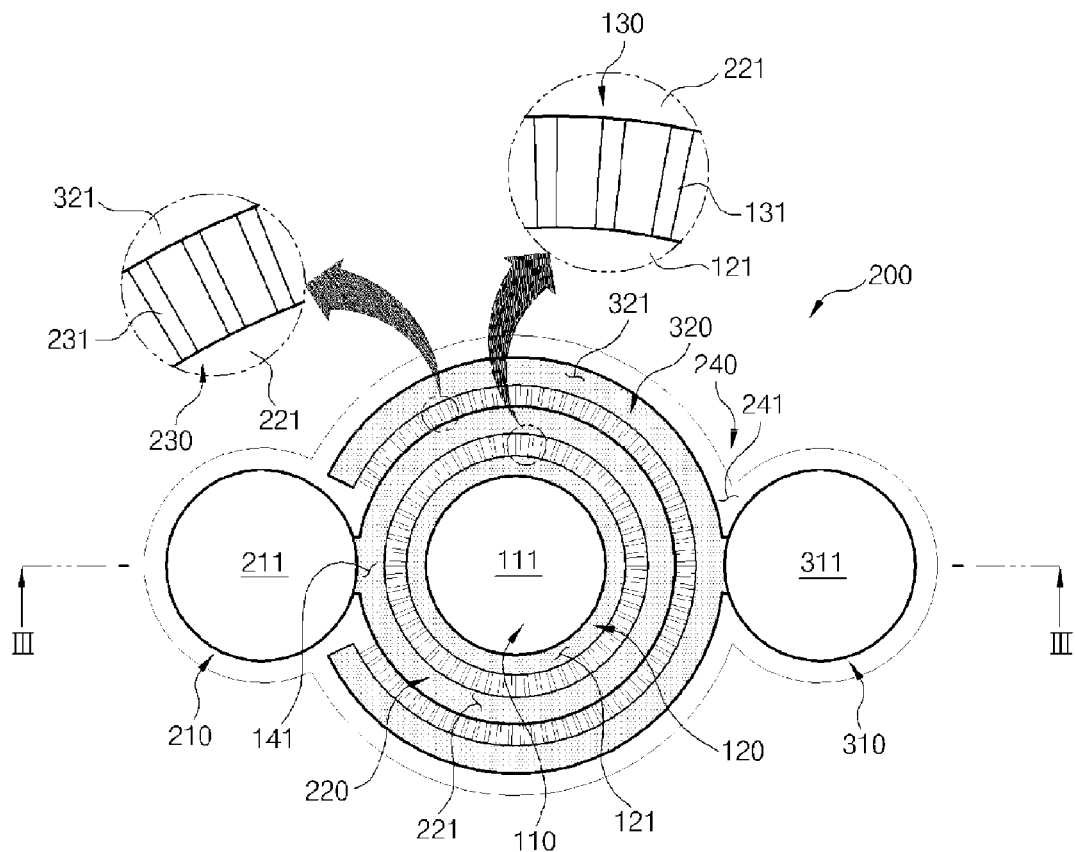
FIG. 6 is a plan view of a microfluidic platform according to another embodiment of the present invention.
Figure 7:
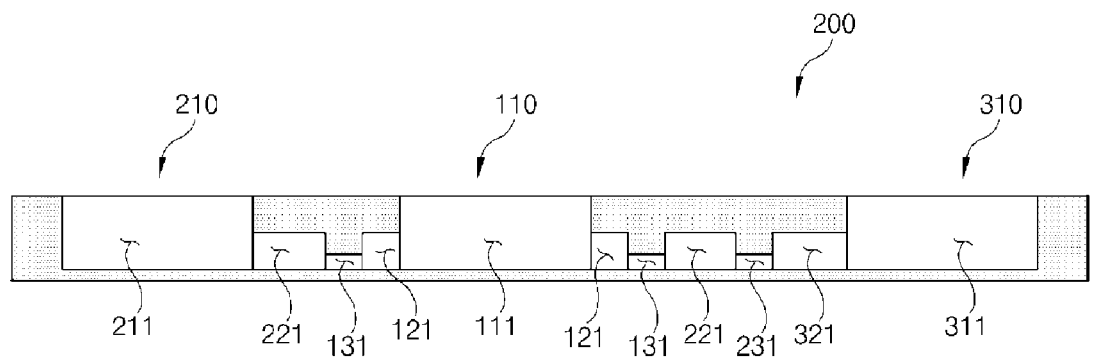
FIG. 7 is a cross-sectional view taken along a line III-III of FIG. 6.

FIG. 6 is a plan view of the microfluidic platform 200 according to the other embodiment of the present invention, and FIG. 7 is a cross-sectional view taken along a line III-III of FIG. 6. Here, like reference numerals in FIGS. 4 through 7 denote like elements that have same operations and effects, and thus overlapping descriptions are not repeated here.

Referring to FIGS. 1, 6, and 7, the microfluidic platform 200 according to the current embodiment further includes, in addition to the components included in the microfluidic platform 100, at least one third reservoir 310, a third compartment 320, a second channel unit 230, and a second communicating unit 240.

The third reservoir 310 includes a third supply unit 311 that has an annular empty space with an opened top surface such that a third cell to be cultured and a culture medium are supplied. Here as well, the third reservoir 310 is a place in which the third cell to be cultured is put and where the culture medium is substantially supplied and replaced. Meanwhile, the third reservoir 310 may be disposed to face the second reservoir 210 based on the first reservoir 110.

The third compartment 320 includes a third culture unit 321 that communicates with the third supply unit 311 and has a partially annular empty space by surrounding a portion of the second compartment at an interval. In the third culture unit 321, the third cell supplied from the third supply unit 311 is cultured in the culture medium. Also, the third compartment 320 has a height of about 100 μm, and is a space where the third cell is stably cultured.

In the second channel unit 230, a plurality of second microchannels 231 communicating the second compartment 220 and the third compartment 320 are annularly arranged. Here, when the second and third cells are neurons, the axon 3 grown by culturing the neuron passes through the second microchannel 231. Here, if a width and height of the second microchannel 231 are high, the neuron at the initial culturing may move to the third compartment 320 on the opposite side. Thus, the second microchannel 231 may have a height from about 2.5 to about 3 μm, a width per channel of about 10 μm, and a width of about 500 to 600 μm so as to prevent the neuron from moving to the third compartment 320. In other words, in the third compartment 320, the axon 3 that passed through the second microchannel 231 of the second channel unit 230 is located.

The second communicating unit 240 includes a second communicating path 241 that communicates the third reservoir 310 and the third compartment 320. Accordingly, the third cell supplied to the third reservoir 310 moves to the third compartment 320 through the second communicating path 241 of the second communicating unit 240 with the culture medium to be cultured.

FIGS. 8 through 11 are plan views of microfluidic platforms 300 through 500 according to other embodiments of the present invention, wherein arrangements of reservoirs are changed from the microfluidic platform 200 of FIGS. 6 and 7. Here, like reference numerals in FIGS. 4 through 11 denote like elements that have same operations and effects, and thus overlapping descriptions are not repeated here.

Figure 8:
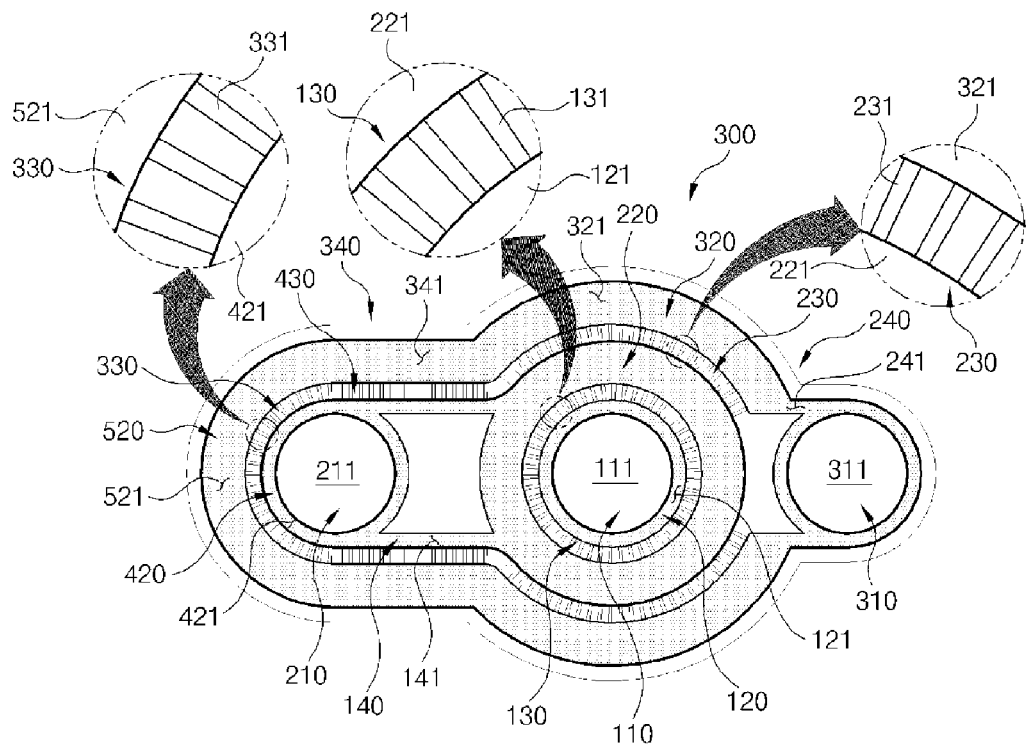
FIGS. 8 through 11 are plan views of microfluidic platforms according to other embodiments of the present invention, wherein arrangements of reservoirs are changed from the microfluidic platform of FIGS. 6 and 7.

First, referring to FIGS. 1 and 8, like the microfluidic platform 200, in the microfluidic platform 300, the second reservoir 210 and the third reservoir 310 face each other based on the first reservoir 110.

Also, the microfluidic platform 300 further includes a fourth compartment 420, a fifth compartment 520, a third channel unit 330, and a third communicating unit 340.

The fourth compartment 420 includes a fourth culture unit 421 that has a partially annular empty space by surrounding a portion of the second supply unit 211 such as to communicate with the second supply unit 211 and the first communicating path 141. Here, in the fourth culture unit 421, the second cell supplied from the second supply unit 211 is cultured in the culture medium. Also, the fourth compartment 420 has a height of about 100 μm and is a space where the second cell is stably cultured.

The fifth compartment 520 includes a fifth culture unit 521 that communicates with the third compartment 320 and has a partially annular empty space by surrounding a portion of the fourth compartment 420 at an interval. In the fifth culture unit 521, the third cell supplied through the fourth compartment 420 is cultured in the culture medium.

In the third channel unit 330, a plurality of third microchannels 331 communicating the fourth compartment 420 and the fifth compartment 520 are annularly arranged. Here, when the second cell is a neuron, the axon 3 grown by culturing the neuron passes through the third microchannel 331. Here, if a width and height of the third microchannel 331 are high, the neuron at the initial culturing may move to the fifth compartment 520 on the opposite side. Thus, the third microchannel 331 may have a height from about 2.5 to about 3 μm, a width of about 10 μm, and a length of about 500 to 600 μm so as to prevent the neuron from moving to the fifth compartment 520. In other words, in the fifth compartment 520, the axon 3 that passed through the third microchannel 331 of the third channel unit 330 is located.

The third communicating unit 340 includes a third communicating path 341 communicating the third compartment 320 and the fifth compartment 520.

Here, the first and third communicating paths 141 and 341 are spaced apart from each other in parallel, and the a fourth channel unit 430 wherein a plurality of fourth microchannels 431 communicating the first and third communicating paths 141 and 341 are annularly arranged may be further included.

In the microfluidic platform 300 described above, when the first through third cells are neurons, not only tertiary neurons sequentially cultured in the first through third compartments 120 through 320, but also secondary neurons cultured in the fourth and fifth compartments 420 and 520 may be viewed together. Accordingly, changes of neurons according to drug treatments under the same conditions may be easily checked.

Next, the microfluidic platform 400 of FIG. 9 will now be described.

As shown in FIG. 9, the microfluidic platform 400 includes a pair of the second reservoirs 210 symmetrically disposed based on the first reservoir 110. Also, a pair of the third reservoirs 310 are symmetrically disposed based on the first reservoir 110. Here, the third reservoirs 310 are disposed on outer sides of the second reservoirs 210 based on the first reservoir 110.

In the microfluidic platform 400 described above, when the first through third cells are neurons, a neuron is supplied to the first reservoir 110 innermostly disposed so as to culture the neuron in the first compartment 120, and after about one week, the axon 3 grown from the neuron passes through the first microchannel 131. After checking the grown axon 3, the neuron is supplied again to the second reservoir 210, and after about one week like the neuron is first supplied to the first reservoir 110, the axon 3 grows towards the third compartment 320 connected to the third reservoir 310. Next, the neuron is supplied again to the third reservoir 310, thereby supplying and culturing the neurons for about 3 weeks through maximum 3 times.

The second reservoirs 210 and the third reservoirs 310 into which the neurons are supplied are in pairs so that air is easily discharged by preparing two spaces for supplying the culture medium, because as described above, after attaching and coating the cover glass, inner spaces (compartments and microchannels) of the microfluidic platform 400 are vacuumed to supply the neurons and the culture medium, and are filled with the culture medium.

Next, the microfluidic platform 400 of FIG. 10 will now be described.

As shown in FIG. 10, in the microfluidic platform 500, the first reservoir 110 and the third reservoir 310 are disposed to face each other based on the second reservoir 210.

Also, in the microfluidic platform 500, additional microchannels are formed between the first and second reservoirs 110 and 210 and between the second and third reservoirs 210 and 310 to experiment and observe various neurons having different growth times.

Lastly, the microfluidic platform 600 of FIG. 11 will now be described.

Figure 11:
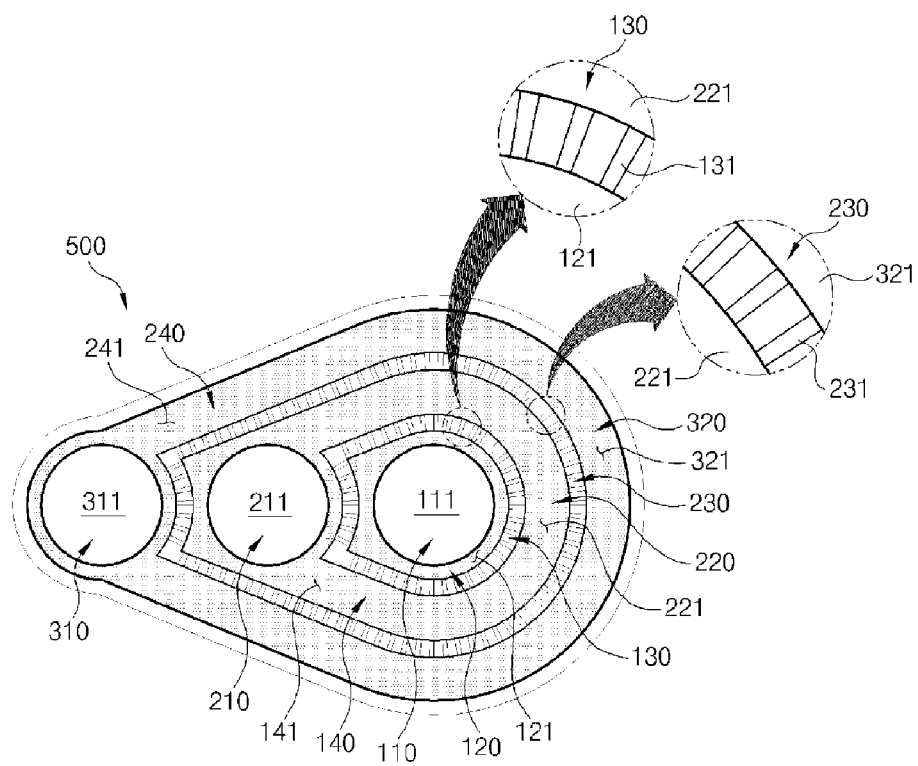

As shown in FIG. 11, in the microfluidic platform 600, the second and third reservoirs 210 and 310 are provided in pairs, and the pairs of second reservoirs 210 and the pairs of the third reservoirs 310 are each symmetrically disposed in a diagonal direction.

Here as well, microchannels are formed between the second and third reservoirs 210 and 310 so as to experiment and observe various neurons having different growth times.

Figure 13:
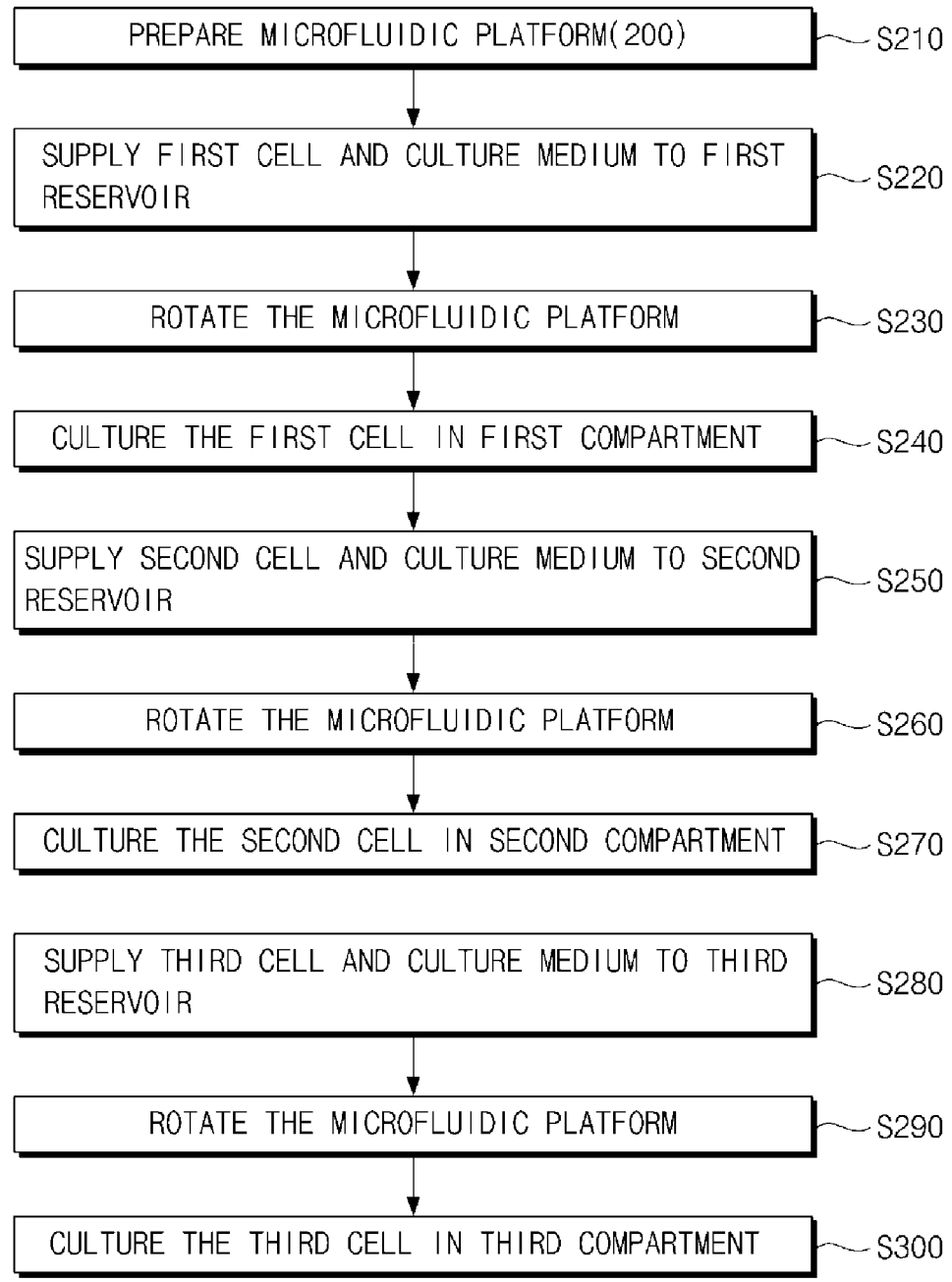
FIG. 13 is a flowchart illustrating a cell culturing method using one of the microfluidic platforms of FIGS. 6 through 11.

A cell culture method using one of the microfluidic platforms 200, 300, 400, 500 and 600, according to an embodiment of the present invention will now be described with reference to FIGS. 6 through 11 and FIG. 13. Here, FIG. 13 is a flowchart illustrating the cell culturing method using one of the microfluidic platforms 200, 300, 400, 500 and 600 of FIGS. 6 through 11.

Referring to FIGS. 1, 6 through 11, and 13, one of the microfluidic platforms 200, 300, 400, 500 and 600 is prepared in operation S210. For convenience of description, it is assumed that the microfluidic platform 200 of FIGS. 6 and 7 is prepared.

When the microfluidic platform 200 is prepared, a first cell and a culture medium are supplied to the first reservoir 110 in operation S220. Here, the first cell may be an initial neuron having a round millet shape, and at this time, the first cell may be the cell body 1 including the nucleus 1a. Also, the inside of the microfluidic platform 200 maintains a wet state during a following culture process.

Then, the microfluidic platform 200 is rotated to generate a centrifugal force. Accordingly, the first cell supplied to the first reservoir 110 is moved to be adjacent to the first microchannel 131 of the first channel unit 130 in the first compartment 120, in operation S230. The microfluidic platform 200 is rotated by using a turn table, but a device for rotating the microfluidic platform 200 is not limited as long as the microfluidic platform 200 is rotated at a uniform speed.

Next, the first cell is cultured in the first compartment 120 in operation S240. When the first cell is a neuron, the axon 3 of the neuron cultured in the first compartment 120 grows and passes through the first microchannel 131 of the first channel unit 130. The axon 3 that passed through the first microchannel 131 as such is located in the second compartment 220.

After about one week after supplying the first cell to the first reservoir 110 and culturing the first cell in the first compartment 120, a second cell and a culture medium are supplied to the second reservoir 210 in operation S250. Here as well, the first cell may be an initial neuron having a round millet shape, and the inside of the microfluidic platform 200 may maintain a wet state during a following culture process.

Then, the microfluidic platform 200 is rotated to generate a centrifugal force such that the second cell supplied to the second reservoir 210 is moved adjacent to the second microchannel 231 of the second channel unit 230 in the second compartment 220, in operation S260. Here as well, the microfluidic platform 200 is rotated by using a turn table, but a device for rotating the microfluidic platform 200 is not limited as long as the microfluidic platform 200 is rotated at a uniform speed.

Next, the second cell is cultured in the second compartment 220 in operation S270. Here as well, when the second cell is a neuron, the axon 3 of the neuron cultured in the second compartment 220 grows and passes through the second microchannel 231 of the second channel unit 230. Also, the dendrite 2 grown from the cell body 1 in the second compartment 220 forms a synapse with the axon 3 that passed through the first microchannel 131 in the first compartment 120.

After about one week after the second cell is supplied to the second reservoir 210 and cultured in the second compartment 220, a third cell and a culture medium are supplied to the third reservoir 310 in operation S280. Here as well, the third cell may be an initial neuron having a round millet shape, and the inside of the microfluidic platform 200 may maintain a wet state during a following culture process.

Then, the microfluidic platform 200 is rotated to generate a centrifugal force so as to move the third cell supplied to the third reservoir 310 to be spaced apart from the second microchannel 231 of the second channel unit 230 in the third compartment 320, in operation S290. Here as well, the microfluidic platform 200 is rotated by using a turn table, but a device for rotating the microfluidic platform 200 is not limited as long as the microfluidic platform 200 is rotated at a uniform speed.

Lastly, the third cell is cultured in the third compartment 320 in operation S300. Here as well, when the third cell is a neuron, the dendrite 2 grown from the cell body 1 in the third compartment forms a synapse with the axon 3 that passed through the second microchannel 231 in the second compartment 220.

As described above, according to the cell culturing method using one of the microfluidic platforms 200, 300, 400, 500 and 600, a probability of observing the cells, for example, the axons 3 of the neurons, that are cultured and grown, may be increased as the first through third compartments 120 through 320 surround at least a portion of the first reservoir 110, the first cells are adjacent to the first microchannel 131 by the centrifugal force generated by rotating one of the microfluidic platforms 200, 300, 400, 500 and 600, the second cells are spaced apart from the first microchannel 131 and adjacent to the second microchannel 231, and the third cells sequentially move to be spaced apart from the second microchannel 231. Also, since a probability of growing cells to correspond to a signal transfer direction of the cells is high, it is easily to secure an experiment target required for an experiment. In other words, in case of a neuron, In other words, in case of the neuron, an experimental observation target for sequentially forming synapses between the axons 3 and the dendrites 2 according to the signal transfer direction may be easily secured. Moreover, by forming microchannels having various shapes between the second reservoir 210 and the third reservoir 310, various neurons having different growth times may be experimented and observed, and also changes of neurons according to drug treatments under the same conditions may be easily observed.

Meanwhile, the insides of the microfluidic platforms 200, 300, 400, 500 and 600 have to maintain a wet state during a culture process. Thus, an amount of the culture medium supplied to the first reservoir 110 is set to be higher than an amount of the culture medium supplied to the second reservoir 210, and the amount of the culture medium supplied to the second reservoir 210 is set to be higher than an amount of the culture medium supplied to the third reservoir 310 so that a flow of the culture medium is maintained in an order of the first through third compartments 120 through 320. For example, the amount of the culture medium supplied to the second reservoir 210 may be less than the amount of the culture medium supplied to the first reservoir 110 by about 10%, and the amount of the culture medium supplied to the third reservoir 310 may be less than the amount of the culture medium supplied to the second reservoir 210 by about 10%.

While the present invention has been particularly shown and described with reference to exemplary embodiments thereof, it will be understood by those of ordinary skill in the art that various changes in form and details may be made therein without departing from the spirit and scope of the present invention as defined by the following claims.

EXPLANATION OF REFERENCE NUMERALS

2: Dendrite 3: Axon
110, 210, 310: First, second, and third reservoirs
111, 211, 311: First, second, and third supply units
120, 220, 320, 420, 520: First, second, third, fourth, and fifth compartments
121, 221, 321, 421, 521: First, second, third, fourth, and fifth culture units
130, 230, 330, 430: First, second, third, and fourth channel units
131, 231, 331, 431: First, second, third, and fourth microchannels
140, 240, 340: First, second, and third communicating units
141, 241, 341: First, second, and third communicating paths

The invention claimed is:

1. A microfluidic platform for cell culturing, comprising:
a first reservoir comprising a first supply unit that has an annular empty space with an opened top surface such that a first cell to be cultured and a culture medium are supplied;
a first compartment comprising a first culture unit that has an annular empty space surrounding at least a portion of the first supply unit to communicate with the first supply unit such that the first cell supplied from the first supply unit is cultured in the culture medium;
at least one second reservoir disposed at one side of the first reservoir and comprising a second supply unit that has an annular empty space with an opened top surface such that a second cell to be cultured and a culture medium are supplied;
a second compartment comprising a second culture unit that communicates with the second supply unit and has a partially annular empty space by surrounding a portion of the first compartment at an interval such that the second cell supplied from the second supply unit is cultured in the culture medium;
a first channel unit wherein a plurality of first microchannels communicating the first compartment and the second compartment are annularly arranged;
a first communicating unit comprising a first communicating path communicating the at least one second reservoir and the second compartment;
at least one third reservoir disposed at the other side of the first reservoir and comprising a third supply unit that has an annular empty space with an opened top surface such that a third cell to be cultured and a culture medium are supplied;
a third compartment comprising a third culture unit that communicates with the third supply unit and has a partially annular empty space by surrounding a portion of the second compartment at an interval such that the third cell supplied from the third supply unit is cultured in the culture medium;
a second channel unit wherein a plurality of second microchannels communicating the second compartment and the third compartment are annularly arranged; and
a second communicating unit comprising a second communicating path communicating the at least one third reservoir and the third compartment.

2. The microfluidic platform of claim 1, wherein the at least one second reservoir and the at least one third reservoir face each other based on the first reservoir.

3. The microfluidic platform of claim 2, further comprising:
a fourth compartment comprising a fourth culture unit that communicates with each of the second supply unit and the first communicating path, and has a partially annular empty space by surrounding a portion of the second supply unit such that the second cell supplied from the second supply unit is cultured in the culture medium;
a fifth compartment comprising a fifth culture unit that communicates with the third compartment and has a partially annular empty space by surrounding a portion of the fourth compartment at an interval such that the third cell supplied through the fourth compartment is cultured in the culture medium;
a third channel unit wherein a plurality of third microchannels communicating the fourth compartment and the fifth compartment are annularly arranged; and
a third communicating unit comprising a third communicating path communicating the third compartment and the fifth compartment.

4. The microfluidic platform of claim 3, wherein the first communicating path and the third communicating path are spaced apart from each other in parallel, and
the microfluidic platform further comprises a fourth channel unit wherein a plurality of fourth microchannels communicating the first communicating path and the third communicating path are annularly arranged.

5. The microfluidic platform of claim 1, wherein a number of the at least one second reservoir is two that are symmetrically arranged based on the first reservoir.

6. The microfluidic platform of claim 5, wherein a number of at least third reservoir is two that are symmetrically arranged based on the first reservoir.

7. The microfluidic platform of claim 6, wherein the at least one third reservoir is disposed on outer sides of the at least one second reservoir based on the first reservoir.

8. The microfluidic platform of claim 1, wherein the first reservoir and the at least one third reservoir face each other based on the at least one second reservoir.

9. The microfluidic platform of claim 1, wherein the first through third cells are neurons.

10. A cell culturing method comprising:
preparing the microfluidic platform of claim 1;
supplying a first cell and a culture medium to the first reservoir;
moving the first cell supplied from the first reservoir to be adjacent to the first microchannel of the first channel unit from the first compartment by rotating the microfluidic platform to generate a centrifugal force;
culturing the first cell in the first compartment;
supplying a second cell and a culture medium to the at least one second reservoir;
moving the second cell supplied from the at least one second reservoir to be spaced apart from the first microchannel of the first channel unit from the second compartment by rotating the microfluidic platform to generate a centrifugal force; and
culturing the second cell in the second compartment.

11. The cell culturing method of claim 10, wherein an amount of the culture medium supplied to the first reservoir is higher than an amount of the culture medium supplied to the at least one second reservoir such that a flow of the culture medium from the first compartment to the second compartment is maintained.

12. The cell culturing method of claim 10, wherein the first and second cells are neurons, and an axon of a neuron cultured in the first compartment grows towards the second compartment through the first microchannel of the first channel unit.

13. A cell culturing method comprising:
preparing the microfluidic platform of claim 1;
supplying a first cell and a culture medium to the first reservoir;
moving the first cell supplied to the first reservoir to be adjacent to the first microchannel of the first channel unit from the first compartment by rotating the microfluidic platform to generate a centrifugal force;
culturing the first cell in the first compartment;
supplying a second cell and a culture medium to the at least one second reservoir;
moving the second cell supplied to the at least one second reservoir to be adjacent to the second microchannel of the second channel unit from the second compartment by rotating the microfluidic platform to generate a centrifugal force;
culturing the second cell in the second compartment;
supplying a third cell and a culture medium to the at least one third reservoir;
moving the third cell supplied to the at least one third reservoir to be spaced apart from the second microchannel of the second channel unit from the second compartment by rotating the microfluidic platform to generate a centrifugal force; and
culturing the third cell in the third compartment.

14. The cell culturing method of claim 13, wherein an amount of the culture medium supplied to the first reservoir is higher than an amount of the culture medium supplied to the at least one second reservoir, and the amount of the culture medium supplied to the at least one second reservoir is higher than an amount of the culture medium supplied to the at least one third reservoir such that a flow of the culture medium is sequentially maintained in an order of the first compartment, the second compartment, and the third compartment.

15. The cell culturing method of claim 13, wherein the first through third cells are neurons,
an axon of a neuron cultured in the first compartment grows towards the second compartment through the first microchannel of the first channel unit to form a synapse with a dendrite of a neuron cultured in the second compartment, and
an axon of the neuron cultured in the second compartment grows towards the third compartment through the second microchannel of the second channel unit.

16. The cell culturing method of claim 11, wherein the first and second cells are neurons, and an axon of a neuron cultured in the first compartment grows towards the second compartment through the first microchannel of the first channel unit.

17. The cell culturing method of claim 14, wherein the first through third cells are neurons,
an axon of a neuron cultured in the first compartment grows towards the second compartment through the first microchannel of the first channel unit to form a synapse with a dendrite of a neuron cultured in the second compartment, and
an axon of the neuron cultured in the second compartment grows towards the third compartment through the second microchannel of the second channel unit.

* * * * *